United States Patent [19]

Sera et al.

[11] 4,066,636
[45] Jan. 3, 1978

[54] METHOD OF HARDENING GELATIN
[75] Inventors: Hidefumi Sera; Kameji Nagao, both of Minami-ashigara, Japan
[73] Assignee: Fuji Photo Film Co., Ltd., Kanagawa, Japan
[21] Appl. No.: 764,507
[22] Filed: Feb. 1, 1977
[30] Foreign Application Priority Data
Feb. 2, 1976 Japan .................................. 51-10541
[51] Int. Cl.² .............................................. C09H 7/00
[52] U.S. Cl. ...................................... 260/117; 96/111; 106/125; 260/8
[58] Field of Search .................... 260/117, 8; 106/125; 96/111

[56] References Cited
U.S. PATENT DOCUMENTS 3,455,892  7/1969  Froehlich .............................. 260/117
4,028,320  6/1977  Sera et al. ............................. 260/117

Primary Examiner—Howard E. Schain
Attorney, Agent, or Firm—Sughrue, Rothwell, Mion, Zinn and Macpeak

[57] ABSTRACT

A method of hardening gelatin which comprises treating gelatin with a compound represented by the formula (I):

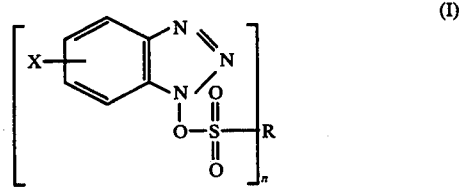

wherein X represents a hydrogen atom, an alkyl group having 6 or less carbon atoms, an aryl group having 8 or less carbon atoms, a haloalkyl group having 2 or less carbon atoms, an alkoxy group having 10 or less carbon atoms, a halogen atom, a carboxy group, a sulfo group, a salt, an alkyl ester having 4 or less carbon atoms in the alkyl moiety or an amide of said carboxy or sulfo group, an acylamino group or a nitro group, $n$ represents 1 or 2, and R represents a monovalent or divalent organic group.

7 Claims, No Drawings

METHOD OF HARDENING GELATIN

BACKGROUND OF THE INVENTION

1. Field of the Invention

The present invention relates to a method of hardening gelatin using an improved hardening agent and particularly to a method of hardening gelatin for silver halide photographic light-sensitive materials.

2. Description of the Prior Art

Gelatin is used as binders for many kinds of photographic light-sensitive materials. For example, the gelatin is used as a main component for silver halide light-sensitive emulsion layers, emulsion protective layers, filter layers, intermediate layers, antihalation layers, backing layers, subbing layers of film bases or baryta layers, etc.

These light-sensitive materials containing the gelatin are processed with various kinds of aqueous solutions, each with a different pH or with a different temperature. The properties of layers containing gelatin which is not processed with a hardening agent depend mainly upon the properties of the gelatin, and such layers have a poor water resistance and the mechanical strength of such layers becomes very low due to excessive swelling in the aqueous solutions. Particularly, in extreme cases, the gelatin layers sometimes dissolve off into the solutions when aqueous solutions at a temperature higher than about 30° C or highly alkaline aqueous solutions are used. These characteristics are fatal defects for layers in photographic light-sensitive materials.

It is known that many compounds are effective for hardening gelatin to improve the water resistance properties, heat resistance properties and scratch resistance properties of gelatin layers.

These compounds are well known as "hardening agents" used in production of photographic light-sensitive materials. For example, aldehyde compounds such as formaldehyde or glutaraldehyde, reactive halogen containing compounds described in U.S. Pat. No. 3,288,775, et al., compounds having ethylenically unsaturated reactive bonds described in U.S. Pat. No. 3,635,718, et al., aziridine compounds described in U.S. Pat. No. 3,017,280, epoxy compounds described in U.S. Pat. No. 3,091,537, halocarboxyaldehydes such as mucochloric acid, dioxanes such as dihydroxydioxane or dichlorodioxane, and inorganic hardening agents, such as chromium alum or zirconium sulfate, etc., are known as gelatin hardening agents.

However, all of these known compounds have some defects. Namely, some have an insufficient hardening function when used for photographic light-sensitive materials, some cause change to occur in quality with the lapse of time because of a hardening function called "post-hardening" which occurs due to a slow hardening reaction with gelatin, some compounds adversely influence the properties of the photographic light-sensitive materials (particularly, increase fogging and reduce sensitivity, etc.), some lose their hardening ability when certain photographic additives are present at the same time or result in a reduction in the functions of these other photographic additives (for example, couplers for color light-sensitive materials), some are difficult to synthesize in a large quantity and some have poor storability because they are unstable themselves.

SUMMARY OF THE INVENTION

An object of the present invention is to provide a novel method for hardening gelatin.

Another object of the present invention is to provide a gelatin hardening agent having an immediate effect for producing photographic light-sensitive materials having stable properties, namely, a low swelling rate and a small degree of swelling of the layers of the light-sensitive materials and very small variations of sensitivity and color balance with the lapse of time.

A further object of the present invention is to provide a novel hardening agent which provides gelatin with excellent water resistance properties, excellent heat resistance properties and excellent scratch resistance properties (particularly, improvements in these characteristics in aqueous solutions at above about 30° C) without adversely influencing the other properties of photographic light-sensitive materials.

These objects are attained by processing the gelatin with compounds represented by the following formula (I):

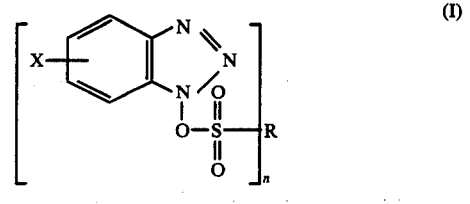

wherein

X represents a hydrogen atom; an alkyl group having 6 or less carbon atoms; an aryl group having 6 to 8 carbon atoms; a haloalkyl group having 1 to 2 carbon atoms; an alkoxy group having 10 or less carbon atoms; a halogen atom; a carboxy group; a sulfo group; a salt, an alkyl ester having 4 or less carbon atoms in the alkyl moiety thereof or an amide of said carboxy and sulfo group; an acylamino group; or a nitro group;

$n$ represents 1 or 2; and

R represents a monovalent or divalent organic group.

DETAILED DESCRIPTION OF THE INVENTION

In the above general formula (I), X represents an alkyl group having 6 or less carbon atoms, such as methyl or ethyl, etc., an aryl group having 6 to 8 carbon atoms, such as phenyl or tolyl, etc., a haloalkyl group having 2 or less carbon atoms, such as trifluoromethyl, etc., an alkoxy group having 10 or less carbon atoms, such as methoxy, ethoxy or benzyloxy, etc., a halogen atom, such as chlorine or bromine, etc., a carboxyl group or a sulfo group or a salt (e.g., the sodium salt, the potassium salt, etc.) of a carboxyl group or a sulfo group, an alkyl ester (e.g., the methyl ester, the ethyl ester, etc.) of a carboxyl group or a sulfo group (wherein the alykl moiety has 4 or less carbon atoms), or an amide (e.g., the dimethylamide, the diethylamide, etc.) of a carboxyl group or a sulfo group, an acylamino group having 8 or less carbon atoms, such as acetylamino, propionylamino, etc., or a nitro group, or a hydrogen atom.

As described above, R may represent any group as long as such group is a monovalent or divalent group, but an alkyl group having 10 or less carbon atoms, such as a methyl, ethyl, propyl, etc., group, an alkylene group having 1 to 8 carbon atoms, such as an ethylene, trimethylene, tetramethylene, etc., group, an aryl group, an aralkyl group, an alkoxy group or a heterocyclic group, such as pyridyl, etc., is preferred, each of which may be substituted with one or more halogen atoms, such as a chlorine atom, a bromine atom, etc.

Of the above-described compounds of the formula (I), particularly preferred compounds are those wherein X represents a hydrogen atom, a chlorine atom or an alkoxy group having 2 or less carbon atoms and R represents an alkylene group having 10 or less carbon atoms, an arylene group or a halogenated arylene group.

The compounds of the formula (I) used in the present invention are known and can be synthesized in good yield according to known general processes. More specifically, they can be synthesized by a dehydrochlorination by reacting at about −60° C to 100° C a corresponding sulfonic acid chloride with a corresponding 1-hydroxybenzotriazole compound in an aprotic solvent, such as benzene, tetrahydrofuran, acetone, chloroform, etc., in the presence of a tertiary amine, such as triethylamine, pyridine or 1,4-diazabicyclo-(2,2,2)-undecene or by a dehydrochlorination in water or an alcohol such as ethanol as the solvent in the presence of an alkali metal hydroxide, such as sodium hydroxide or potassium hydroxide or a salt of a weak acid such as carbonate (e.g., sodium carbonate, potassium carbonate, etc.), etc.

Examples of compounds of the formula (I) which can be used in the present invention are described below. However, the present invention is not to be construed as being limited to these examples.

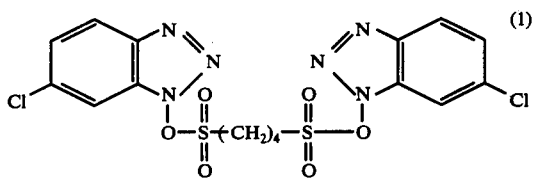
(1)

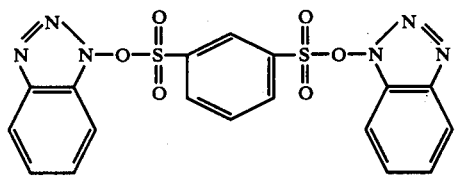
(2)

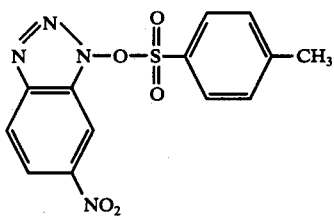
(3)

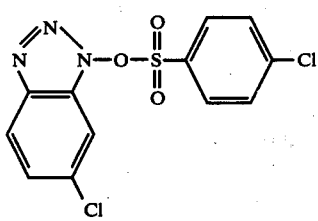
(4)

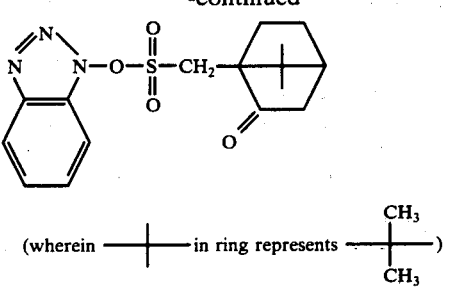
(5)

(wherein ─┼─ in ring represents ─┼─C(CH₃)₂─)

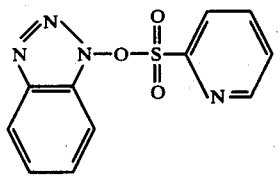
(6)

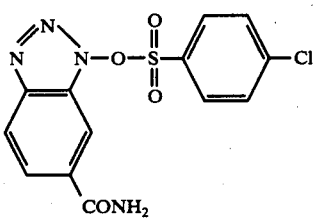
(7)

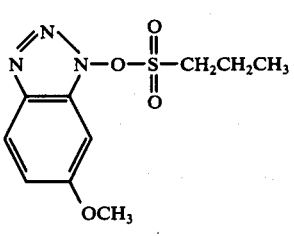
(8)

The strength of the gelatin films in the photographic light-sensitive materials produced using the hardening agent of the present invention is established just after production of the light-sensitive materials, because the hardening agent of the present invention causes a rapid hardening reaction to occur and a post-hardening phenomenon does not occur using the hardening agent of the present invention. Accordingly, if the properties of the light-sensitive materials just after production are compared with those of light-sensitive materials after the lapse of a long time, there is no difference in apparent sensitivity and color balance caused by a difference in penetration rates of developing agents.

Further, the hardening agent used in the present invention does not cause the viscosity of gelatin solutions to increase before such are used to form films by coating after the hardening agent has been added thereto, because although the hardening agent causes a suitable hardening reaction to occur nevertheless it does not cause a post-hardening phenomenon to occur. Consequently, the hardening agent can be advantageously used for mass production of photographic light-sensitive materials.

Further, the hardening agent used in the present invention does not cause the effect of other photographic additives also present, such as couplers for color photographic light-sensitive materials, to be reduced by interaction with them nor is the hardening function of the hardening agent lost. Moreover, the hardening agent does not adversely influence the properties of the photographic light-sensitive materials (particularly, increase fogging and reduce sensitivity).

The amount of the hardening agent used in the present invention when such is incorporated in a gelatin layer of a photographic material can be suitably chosen depending on the purpose. Generally, a suitable amount ranges from about 0.05 to about 30%, preferably 0.1 to 20%, by weight based on the weight of dry gelatin. A most preferred amount ranges from 0.5 to 10% by weight. If the amount of the hardening agent of this invention is above about 30% by weight based on the dry gelatin, it becomes impossible to form films from the aqueous solution of gelatin by, for example, coating or spray coating, because the aqueous solution of gelatin sometimes gelatinizes and hardens. On the other hand, if the amount is below about 0.05% by weight, although formation of the films can be carried out using the aqueous solution of gelatin, the resulting films do not sufficiently harden after drying and the strength of such films is insufficient. On the contrary, when the amount of the hardening agent is within the above-described range, the property of rapid hardening of the gelatin, which is a characteristic of the present invention, is sufficiently exhibited.

The hardening agent of the present invention can be used individually or two or more hardening agents of the present invention may be used as a mixture. Further, the hardening agent of this invention can be used together with other known hardening agents. Examples of known hardening agents with which the hardening agent can be used are, for example, aldehyde compounds, such as formaldehyde or glutaraldehyde, ketone compounds, such as diacetyl or cyclopentanedione, bis(2-chloroethylurea), 2-hydroxy-4,6-dichloro-1,3,5-triazine, reactive halogen containing compounds described in U.S. Pat. Nos. 3,288,775 and 2,732,303 and British Pat. Nos. 974,723 and 1,167,207, etc., divinylsulfone, 5-acetyl-1,3-diacryloylhexahydro-1,3,5-triazine, reactive olefinic compounds described in U.S. Pat. Nos. 3,635,718 and 3,232,763 and British Pat. No. 994,869, N-hydroxymethylphthalimide, N-methylol compounds described in U.S. Pat. Nos. 2,732,316 and 2,586,168, isocyanates described in U.S. Pat. No. 3,103,437, aziridine compounds described in U.S. Pat. Nos. 3,017,280 and 2,983,611, acid derivatives described in U.S. Pat. Nos. 2,725,294 and 2,725,295, carbodiimide compounds described in U.S. Pat. No. 3,100,704, epoxy compounds described in U.S. Pat. No. 3,091,537, isoxazole compounds described in U.S. Pat. Nos. 3,321,313 and 3,543,292, halocarboxyaldehydes, such as mucochloric acid, dioxane derivatives, such as dihydroxydioxane or dichlorodioxane, and inorganic hardening agents, such as chromium alum or zirconium sulfate, etc. Further, the hardening agents used in this invention can be used together with precursor type compounds, such as alkali metal bisulfite-aldehyde addition products, methylol derivatives of hydantoin or monohydric aliphatic nitroalcohols, etc. When the hardening agent of the present invention is used together with other hardening agent(s), the ratio thereof can be appropriately chosen depending on the purpose or effect desired.

Where the compounds of the present invention are used for light-sensitive layers of silver halide light-sensitive materials, any silver halide may be used. Namely, any of silver chloride, silver bromide, silver bromochloride, silver bromoiodide and silver iodobromochloride may be used without any limitation as to production, crystal habit or particle size of the silver halide.

The silver halide emulsions can be sensitized using conventional chemical sensitizers, such as gold compounds, such as chloroaurate or gold trichloride, etc., noble metal salts, such as a salt or platinum, palladium or iridium, etc., or sulfur compounds which form silver sulfide by reacting with silver salts.

Further, sensitizing dyes can be added to the silver halide emulsions and suitable sensitizing dyes can be chosen depending on the wavelength range to which the silver halide is to be sensitized, the sensitivity of use of the light-sensitive material, etc.

For the purpose of preventing a reduction in sensitivity and an occurrence of fog during preparation of the light-sensitive materials, during storage or during processing of the light-sensitive materials, various kinds of compounds may be added to the above-described photographic emulsions. Many known compounds, for example, heterocyclic compounds, mercury containing compounds, mercapto compounds, metal salts as well as 4-hydroxy-6-methyl-1,3,3a,7-tetrazaindene, 3-methylbenzothiazole and 1-phenyl-5-mercaptotetrazole can be used for such purposes.

Examples of suitable compounds capable of achieving the above are described in C. E. K. Mees and T. H. James, *The Theory of the Photographic Process*, 3rd Ed., pages 344 – 349, Macmillan Co., New York (1966) and in the following patents: U.S. Pat. Nos. 1,758,576, 2,110,178, 2,131,038, 2,173,628, 2,697,040, 2,304,962, 2,324,123, 2,394,198, 2,444,605 - 8, 2,566,245, 2,694,716, 2,697,099, 2,708,162, 2,728,663 - 5, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,688 and 3,622,339 and British Pat. Nos. 893,428, 403,789, 1,173,609 and 1,200,188.

The gelatin to which the hardening agent of the present invention can be applied includes the so-called alkali treated (lime treated) gelatin which is prepared by treatment in an alkali bath when the gelatin is extracted from collagen, acid treated gelatin which was prepared by treatment in an acid bath and enzyme treated gelatin as described in *Bull. Soc. Sci. Photo. Japan*, No. 16, page 30 (1966). Further, the hardening agent of the present invention can be applied to gelatin having a low molecular weight which was prepared by partially hydrolyzing the gelatin in a water bath with heating or by reacting with a protease.

The gelatin to which the hardening agent of the present invention can be applied may be partially replaced, if desired, by colloidal albumin, casein, cellulose derivatives, such as carboxymethyl cellulose or hydroxyethyl cellulose, etc., saccharose derivatives such as agar, sodium alginate or starch derivatives, etc., or synthetic hydrophilic colloids, such as polyvinyl alcohol, poly-N-vinylpyrrolidone, acrylic acid copolymers, polyacrylamide or derivatives thereof or partially hydrolyzed products thereof, and also replaced by the so-called gelatin derivatives, namely, those wherein the amino groups, imino groups, hydroxy groups or carboxyl groups as functional groups in the gelatin molecule are reacted with reactants having a group capable of reacting with such groups or graft polymers prepared by grafting the molecular chain of other high molecular weight materials thereto.

Examples of suitable reactants for producing the above-described gelatin derivatives include isocyanates, acid chlorides and acid anhydrides described in U.S. Pat. No. 2,614,928, acid anhydrides described in U.S. Pat. No. 3,118,766, bromoacetic acids described in Japanese Patent Publication No. 5514/64, phenyl glycidyl ethers described in Japanese Patent Publication No. 26845/67, vinyl sulfone compounds described in U.S. Pat. No. 3,132,945, N-allyl vinylsulfonamides described in British Pat. No. 861,414, maleinimide compounds described in U.S. Pat. No. 3,186,846, acrylonitriles described in U.S. Pat. No. 2,594,293, polyalkylene oxides described in U.S. Pat. No. 3,312,553, epoxy compounds described in Japanese Patent Publication No. 26845/67, acid esters described in U.S. Pat. No. 2,763,639 and alkane sultones described in British Pat. No. 1,033,189, etc.

Many descriptions concerning branching high molecular weight materials suitable for grafting to gelatin appear in U.S. Pat. Nos. 2,763,625, 2,831,767, and 2,956,884, Polymer Letters 5,595 (1967), Phot. Sci. Eng. 9 148 (1965) and J. Polymer Sci. A-1 9 3199 (1971). Polymers and copolymers of the so-called vinyl monomers such as acrylic acid, methacrylic acid or the esters, amides or nitriles thereof, or styrene, etc. can be widely used as such materials. However, hydrophilic vinyl polymers having a certain degree of compatibility with gelatin, such as polymers and copolymers of acrylic acid, acrylamide, methacrylamide, hydroxyalkyl acrylates or hydroxyalkyl methacrylates, etc. are particularly preferred.

The term "gelatin" as used herein and in the appended claims is used to describe the various types of gelatins described above, gelatin derivatives as described above and replacements for gelatin described above.

In using the hardening agent of the present invention for photographic light-sensitive materials, synthetic polymer compounds, such as a latex of water dispersable vinyl polymers and particularly compounds which increase the dimensional stability of the photographic materials may be incorporated into photographic emulsion layers or other layers individually or as a mixture (of different kinds of polymers) or together with hydrophilic water permeable colloids. Examples of such polymers include many kinds of compounds, which are described in, for example, U.S. Pat. Nos. 2,376,005, 2,739,137, 2,853,457, 3,062,674, 3,411,911, 3,488,708, 3,525,620, 3,635,715, 3,607,290, and 3,645,740 and British Pat. Nos. 1,186,699 and 1,307,373. Of these compounds, copolymers and homopolymers of alkyl acrylates, alkyl methacrylates, acrylic acid, methacrylic acid, sulfoalkyl acrylates, sulfoalkyl methacrylate, glycidyl acrylate, glycidyl methacrylate, hydroxyalkyl acrylates, hydroxyalkyl methacrylates, alkoxyalkyl acrylates, alkoxyalkyl methacrylates, styrene, butadiene, vinyl chloride, vinylidene chloride, maleic acid anhydride and itaconic acid anhydride are generally used. If desired, the so-called graft type emulsion polymerization latexes which were prepared by emulsion polymerization of the above described vinyl compounds in the presence of hydrophilic protective colloid high molecular materials may be used.

In using the gelatin hardening agent of the present invention for photographic light-sensitive materials, matting agents can be used together therewith. Examples of suitable matting agents are finely divided particles of water insoluble organic or inorganic compounds having an average particle size of about 0.2 $\mu$ to about 10 $\mu$, and preferably 0.3 $\mu$ to 5 $\mu$. Examples of organic compounds preferably used include water dispersable vinyl polymers, such as polymethyl acrylate, polymethyl methacrylate, polyacrylonitrile, acrylonitrile-α-methylstyrene copolymers, polystyrene, styrenedivinylbenzene copolymers, polyvinyl acetate, polyethylene carbonate and polytetrafluoroethylene, etc., cellulose derivatives, such as methyl cellulose, ethyl cellulose, cellulose acetate and cellulose acetate propionate, etc., starch derivatives, such as carboxymethyl starch, carboxynitrophenyl starch and urea-formaldehyde-starch reaction products, etc., gelatin which was hardened with known hardening agents and hardened gelatin prepared by coacervation to form finely divided capsular particles, etc. Examples of inorganic compounds which are preferably used include silicon dioxide, titanium dioxide, magnesium dioxide, aluminum dioxide, barium sulfate, calcium carbonate, silver chloride desensitized by known methods, silver bromide desensitized in the same manner as described above, and glass, etc. The above-described matting agents can be used, if desired, individually or as a mixture of two or more thereof.

In using the gelatin hardening agent of the present invention for photographic light-sensitive materials, couplers may be also used in combination therewith. In such cases, the so-called non-diffusible couplers are incorporated in silver halide emulsion layers. Examples of couplers which can be used are 4-equivalent diketomethylene type yellow couplers and 2-equivalent diketomethylene type yellow couplers, such as the compounds described in U.S. Pat. Nos. 3,415,652, 3,447,928, 3,311,476 and 3,408,194, etc., the compounds described in U.S. Pat. Nos. 2,875,057, 3,265,506, 3,409,439, 3,551,155, and 3,551,156, etc., and the compounds described in Japanese Patent Application (OPI) No. 26133/72 and Japanese Patent Publication No. 66836/73, etc.; 4-equivalent and 2-equivalent pyrazolone type magenta couplers and imidazolone type magenta couplers, such as the compounds described in U.S. Pat. Nos. 2,600,788, 2,983,608, 3,062,653, 3,214,437, 3,253,924, 3,419,391, 3,419,808, 3,476,560 and 3,582,322, Japanese Patent Publication No. 20636/70 and Japanese Patent Application (OPI) No. 26133/72; and α-naphthol type cyan couplers and phenol type cyan couplers, such as the compounds described in U.S. Pat. Nos. 2,474,293, 2,698,794, 3,034,892, 3,214,437, 3,253,924, 3,311,476, 3,458,315 and 3,591,383 and Japanese Patent Publications No. 11304/67 and 32461/69. In addition, the compounds described in U.S. Pat. Nos. 3,227,554, 3,297,445, 3,253,924, 3,311,476, 3,379,529, 3,516,831, 3,617,291 and 3,705,801 and German Patent Application (OLS) No. 2,163,811 may be used.

Surface active agents may be added, individually or as a mixture thereof, to the photographic emulsions of the photographic light-sensitive materials to which the hardening agent of the present invention is applied. Although surface active agents are generally used as coating assistants, they are sometimes used for other purposes, for example, for emulsification, sensitization, improvement of photographic properties, prevention of electrostatic charging or prevention of adhesion, etc.

These surface active agents can be classified into natural surface active agents, such as saponin, nonionic surface active agents, such as alkylene oxide type, glycerin type, and glycidol type agents, etc., cationic surface active agents, such as higher alkylamines, quaternary ammonium salts, pyridine and other heterocyclic compounds, phosphonium or sulfonium compounds, etc., anionic surface active agents which contain acid groups, such as carboxylic acid, sulfonic acid, phosphoric acid, sulfuric acid ester or phosphoric acid ester groups, etc., and ampholytic surface active agents, such as amino acids, aminosulfonic acids, sulfuric acid esters or phosphoric acid esters of aminoalcohols, etc.

The photographic emulsions are coated on substantially planar support materials, for example, a rigid support, if desired, such as glass, metal or ceramic or a flexible support.

Examples of typical flexible supports include cellulose nitrate films, cellulose acetate films, cellulose acetate butyrate films, cellulose acetate propionate films, polystyrene films, polyethylene terephthalate films, polycarbonate films, laminated films of the above-described films, thin glass films, baryta coated paper, paper laminated or coated with α-olefin polymers and, particularly, with polymers of an α-olefin having 2 to 10 carbon atoms, such as polyethylene, polypropylene or an ethylene-butene copolymer, etc., and plastic films described in Japanese Patent Publication No. 19068/72, the surface of which was roughened so as to improve the adhesive property to other high molecular weight materials and to improve the printability thereof, which have been conventionally used for photographic light-sensitive materials.

In using the hardening agent of the present invention, each layer of the photographic light-sensitive materials can be formed by various kinds of coating methods, such as dip coating, air-knife coating, curtain coating, spray coating or extrusion coating using a hopper described in U.S. Pat. No. 2,681,294.

If desired, two or more layers can be coated at the same time using the methods described in U.S. Pat. Nos. 2,761,791, 3,508,947, 2,941,898 and 3,526,528, etc.

In the method of this invention for hardening gelatin with the gelatin hardening agent of the formula (I) above, the processing of the gelatin or gelatin containing layer can be conducted at substantially any time, e.g., before coating of such a layer, after coating of such a layer, etc. Further, the hardening agent of the present invention may be used by adding such not only to light-sensitive materials but also to processing solutions. Suitable temperatures for the treatment of gelatin or gelatin layers with the hardening agent of this invention can range from about 10° to about 50° C. Where the hardening agent is used in a processing solution, a suitable amount of the hardening agent can range up to about 5% by weight, preferably 0.1 to 3% by weight, based on the processing solution.

Examples of synthesis of the compounds of the formula (I) which can be used in the present invention and examples of the present invention are illustrated in greater detail below. Unless otherwise indicated, all parts, percents, ratios and the like are by weight.

SYNTHESIS EXAMPLE 1

Synthesis of Compound (1)

8.5 g of 1-hydroxy-6-chloro-1,2,3-benzotriazole and 6 g of triethylamine were dissolved in 500 ml of anhydrous acetone. To the resulting solution, a solution containing 6.4 g of tetramethylene disulfonyl chloride in 50 ml of benzene was added dropwise with stirring at 0° – 10° C. After the addition, the temperature was increased to room temperature (about 20° – 30° C) and the mixture was stirred at room temperature for 4 hours and filtered. The filtrate was condensed at a bath temperature of 40° C under a reduced pressure. After such was condensed to a volume of about 100 ml, 600 g of ice water was added thereto and the precipitated crystals were separated by filtration and dried to obtain 6.8 g of white crystals.

Elemental Analysis

|  | C | H | N |
|---|---|---|---|
| Calculated (%): | 36.85 | 2.69 | 16.12 |
| Found (%): | 36.71 | 2.83 | 16.06 |

SYNTHESIS EXAMPLE 2

Synthesis of Compound (3)

9 g of 1-hydroxy-6-nitro-1,2,3-benzotriazole and 3 g of sodium hydroxide were dissolved in 400 ml of water and 10 g of p-toluenesulfonyl chloride was added dropwise thereto with vigorous stirring. After stirring the mixture at 5° C for 3 hours the temperature was increased to room temperature and the mixture was filtered. After recrystallization with a solvent mixture of ethyl acetate and hexane (6:4 by volume), 5 g of yellow crystals was obtained.

Elemental Analysis

|  | C | H | N |
|---|---|---|---|
| Calculated (%): | 46.71 | 3.00 | 16.77 |
| Found (%): | 46.62 | 3.14 | 16.72 |

SYNTHESIS EXAMPLE 3

Synthesis of Compound (5)

8.5 g of 1-hydroxy-6-chloro-1,2,3-benzotriazole and 6 g of triethylamine were dissolved in 500 ml of anhydrous acetone. 7 g of p-chlorobenzenesulfonyl chloride was reacted in the same manner as in Synthesis Example 1 to obtain 9.2 g of white crystals.

Elemental Analysis

|  | C | H | N |
|---|---|---|---|
| Calculated (%): | 41.86 | 2.03 | 12.21 |
| Found (%): | 41.82 | 2.31 | 12.25 |

EXAMPLE 1

To an aqueous solution of gelatin containing 70 g of dry gelatin per liter of solution, the hardening agent of the present invention, as shown in the following table, was added. The mixture was coated uniformly on a cellulose triacetate film support having a subbing layer thereon and dried to form a layer having a dry thickness of about 10 μ. After the resulting sample was stored at 25° C under 55% RH for 20 days, the degree of swelling in water was measured.

The value of the degree of swelling was obtained by measuring the film thickness after immersing the sample in water at 20° C for 10 minutes and dividing the increase in the film thickness by the thickness of the dry film before immersing.

TABLE 1

| Results of Measurement of Degree of Swelling in Example 1 | | | |
|---|---|---|---|
| Hardening Agent | Amount (milli mol/ g gelatin) | Degree of Swelling | Note |
| None | 0 | 10.30 | Control |

TABLE 1-continued
Results of Measurement of Degree of Swelling in Example 1

| Hardening Agent | Amount (milli mol/ g gelatin) | Degree of Swelling | Note |
|---|---|---|---|
| Compound 1 | 0.03 | 3.85 | Present invention |
| Compound 3 | " | 4.50 | " |
| Compound 4 | " | 4.35 | " |
| Compound 7 | " | 4.55 | " |

As can be understood from the results in Table 1, the compounds of the present invention have a cross-linking ability sufficient to prevent excess swelling of the gelatin in water.

EXAMPLE 2

An emulsion prepared by a neutralization process containing 120 g of gelatin and 100 g of silver bromide per kg of the emulsion was divided into the following portions. After adding the hardening agent as described in the following table, each portion was coated uniformly on a cellulose triacetate support having a subbing layer thereon and dried to form a layer having a dry film thickness of about 10 μ. The resulting sample film was stored at 25° C under 55% RH. After 1 day, 3 days, 7 days and 28 days from the coating, the melting point of the emulsion layer in each case was measured. Further, the melting point of the emulsion layer of the sample film which was stored at 50° C under 80% RH for 2 days (accelerated conditions) was measured.

The melting point of the emulsion layer is the temperature at which the swollen emulsion layer began to melt when the sample film is immersed in a 2% aqueous solution of $Na_2CO_3$, the temperature of which was increased from 25° C at a rate of 1° C per minute.

TABLE 2
Results of Measurement of Post-Hardening in Example 2

| Hardening Agent | Amount (milli mol/ g gelatin) | Melting Point (° C) | | | | Accelerated Conditions at 50° C 80% RH for 2 Days |
|---|---|---|---|---|---|---|
| | | 1 Day | 3 Days | 7 Days | 28 Days | |
| None | 0 | 34 | 34 | 34 | 34 | 35 |
| Muco- chloric acid | 0.03 | 63 | 75 | 79 | 83 | 290 |
| Compound 1 | " | 88 | 89 | 89 | 89 | 90 |
| Compound 2 | " | 80 | 82 | 82 | 82 | 84 |
| Compound 6 | " | 79 | 79 | 79 | 79 | 80 |

From the results in Table 2, although mucochloric acid used for comparison had sufficient hardening ability, an undesirable post-hardening, namely, the melting point varies with the lapse of time, occurs with its use. On the contrary, the compounds of the present invention not only have sufficient hardening ability but also very small variation in the melting point with the lapse of time occurs and a preferable hardening function is achieved.

EXAMPLE 3

Coating samples prepared in Example 2 which were stored at 25° C under 55% RH for 30 days and those which were stored under an accelerated condition (50° C, 80% RH) for 2 days were exposed to a light wedge and developed at 20° C for 8 minutes using a developer having the following composition:

| N-Methyl-p-aminophenol Sulfate | 2 g |
|---|---|
| Sodium Sulfite (anhydrous) | 100 g |
| Hydroquinone | 5 g |
| Borax (decahydrate) | 2 g |
| Water to make | 1 l |

These samples were then subjected to sensitometric measurement. The results of these measurements are shown in the Table 3 below.

TABLE 3
Results of Sensitometric Measurement in Example 3

| Hardening Agent | Amount (milli mol/ g gelatin) | Sample Stored under Room Temperature Conditions | | Sample Stored under Accelerated Conditions | |
|---|---|---|---|---|---|
| | | Relative Sensitivity | Fog | Relative Sensitivity | Fog |
| None | 0 | 100 | 0.10 | 100 | 0.20 |
| Mucochloric acid | 0.03 | 93 | 0.08 | 90 | 0.25 |
| Compound 1 | " | 98 | 0.05 | 95 | 0.08 |
| Compound 5 | " | 98 | 0.08 | 93 | 0.08 |
| Compound 7 | " | 95 | 0.10 | 95 | 0.10 |

As can be understood from the results in Table 3, the compounds of the present invention do not adversely influence the photographic properties in a practical manner.

While the invention has been described in detail and with reference to specific embodiments thereof. It will be apparent to one skilled in the art that various changes and modifications can be made therein without departing from the spirit and scope thereof.

What is claimed is:

1. A method of hardening gelatin which comprises treating gelatin with a compound represented by the formula (I):

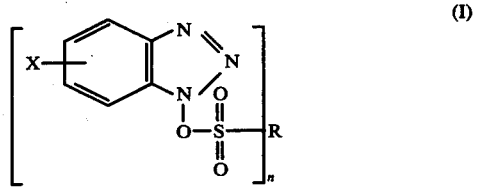

wherein X represents a hydrogen atom, an alkyl group having 6 or less carbon atoms, an aryl group having 6 to 8 carbon atoms, a haloalkyl group having 1 to 2 carbon atoms, an alkoxy group having 10 or less carbon atoms, a halogen atom, a carboxy group, a sulfo group, a salt of a carboxy group or a sulfo group, an alkyl ester having 4 or less carbon atoms in the alkyl moiety or an amide of said carboxy and sulfo group, an acylamino group or a nitro group, $n$ represents 1 or 2, and R represents a monovalent or divalent organic group.

2. The method of claim 1, wherein X is a hydrogen atom, a methyl group, an ethyl group, a phenyl group, a tolyl group, a trifluoromethyl group, a methoxy group, an ethoxy group, a benzyloxy group, a chlorine atom, or a bromine atom.

3. The method of claim 1, wherein R is an alkyl group having 10 or less carbon atoms, an alkylene group, an aralkyl group, an alkoxy group or a heterocyclic group, which may be unsubstituted or substituted with one or more halogen atoms.

4. The method of claim 1, wherein X is a hydrogen atom or a halogen atom; and R is an alkylene group having 1 to 8 carbon atoms.

5. The method of claim 1, wherein the compound represented by the formula (I) is incorporated into a gelatin layer and the amount of the compound represented by the formula (I) to the gelatin ranges from about 0.05 to about 30% weight based on the weight of the dry gelatin.

6. The method of claim 1, wherein said treating of gelatin is with a processing solution containing the compound represented by the formula (I) and the processing solution contains about 5% by weight or less of said compound represented by the formula (I).

7. The method of claim 1, wherein said gelatin is alkali-treated gelatin, acid-treated gelatin, partial hydrolysis products of gelatin, enzymatic decomposition products of gelatin, a gelatin derivative in which the amino groups, imino groups, hydroxy groups or carboxyl groups as functional groups in the gelatin molecule are reacted with other reactants containing a group capable of reacting with such groups, or a graft polymer of gelatin comprising the reaction product obtained on grafting a molecular chain of another high molecular weight material to gelatin.

* * * * *